(12) United States Patent  (10) Patent No.: US 8,002,767 B2
Sanchez et al.  (45) Date of Patent: Aug. 23, 2011

(54) MULTIFUNCTIONAL HANDLE FOR A MEDICAL ROBOTIC SYSTEM

(75) Inventors: Dan Sanchez, Santa Barbara, CA (US); Darrin Uecker, Santa Barbara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1036 days.

(21) Appl. No.: 10/921,061

(22) Filed: Aug. 18, 2004

(65) Prior Publication Data

US 2005/0043719 A1 Feb. 24, 2005

Related U.S. Application Data

(63) Continuation of application No. 10/012,602, filed on Dec. 8, 2001, now Pat. No. 6,793,653.

(51) Int. Cl.
*A61B 17/00* (2006.01)

(52) U.S. Cl. .................... 606/1; 606/45; 606/46

(58) Field of Classification Search .......... 606/1, 41, 606/45, 46, 48–50; 901/2, 3, 23, 29, 30, 901/32, 36, 27, 41; 600/102; 700/260; 414/1
See application file for complete search history.

(56) References Cited

U.S. PATENT DOCUMENTS

| | | |
|---|---|---|
| 977,825 A | 12/1910 | Murphy |
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |

(Continued)

FOREIGN PATENT DOCUMENTS

DE 9204118 7/1992

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner* — Thomas J Sweet
*Assistant Examiner* — Victoria W Chen

(57) ABSTRACT

A handle used to control movement of a medical instrument. The medical instrument may be coupled to a robotic arm that is connected to a controller. The medical instrument may have a plurality of functions such as wrist locking and motion scaling. One of the functions may be selected through a graphical user interface operated by the end user. The handle may have a plurality of buttons. One of the buttons may allow the end user to control the selected function. For example, when wrist locking/unlocking is selected, depressing the button can toggle the medical instrument wrist between a locked state and an unlocked state.

7 Claims, 6 Drawing Sheets

U.S. PATENT DOCUMENTS

| | | |
|---|---|---|
| 4,624,011 A | 11/1986 | Watanabe et al. |
| 4,633,389 A | 12/1986 | Tanaka et al. |
| 4,635,292 A | 1/1987 | Mori et al. |
| 4,635,479 A | 1/1987 | Salisbury, Jr. et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Andersson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,943,296 A * | 7/1990 | Funakubo et al. ............. 606/166 |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,046,375 A | 9/1991 | Salisbury, Jr. et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A * | 4/1992 | Tsuchihashi et al. ......... 700/264 |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,272,497 A * | 12/1993 | Furuya et al. ................. 396/17 |
| 5,279,309 A | 1/1994 | Taylor et al. |
| 5,282,806 A | 2/1994 | Haber et al. |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,373,317 A * | 12/1994 | Salvati et al. .................... 348/65 |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,443,484 A | 8/1995 | Kirsch et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,490,843 A | 2/1996 | Hildwein et al. |
| 5,506,912 A | 4/1996 | Nagasaki et al. |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,727,569 A | 3/1998 | Benetti et al. |
| 5,735,290 A | 4/1998 | Sterman et al. |
| 5,737,500 A * | 4/1998 | Seraji et al. .................... 700/251 |
| 5,737,711 A | 4/1998 | Abe |
| 5,749,362 A | 5/1998 | Funda et al. |
| 5,754,741 A | 5/1998 | Wang et al. |
| 5,762,458 A * | 6/1998 | Wang et al. ........................ 414/1 |
| 5,766,126 A | 6/1998 | Anderson |
| 5,776,126 A | 7/1998 | Wilk et al. |
| 5,779,623 A | 7/1998 | Bonnell |
| 5,784,542 A * | 7/1998 | Ohm et al. ..................... 700/260 |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |

| | | | |
|---|---|---|---|
| 5,814,038 A | 9/1998 | Jensen et al. | |
| 5,817,084 A | 10/1998 | Jensen | |
| 5,825,982 A * | 10/1998 | Wright et al. | 700/259 |
| 5,827,319 A | 10/1998 | Carlson et al. | |
| 5,831,408 A | 11/1998 | Jacobus et al. | |
| 5,836,869 A | 11/1998 | Kudo et al. | |
| 5,844,824 A | 12/1998 | Newman et al. | |
| 5,855,583 A | 1/1999 | Wang et al. | |
| 5,859,934 A | 1/1999 | Green | |
| 5,860,995 A | 1/1999 | Berkelaar | |
| 5,870,035 A * | 2/1999 | Bjernulf | 341/35 |
| 5,876,325 A | 3/1999 | Mizuno et al. | |
| 5,878,193 A | 3/1999 | Wang et al. | |
| 5,882,206 A | 3/1999 | Gillio | |
| 5,887,121 A | 3/1999 | Funda et al. | |
| 5,898,599 A | 4/1999 | Massie et al. | |
| 5,904,702 A | 5/1999 | Ek et al. | |
| 5,906,630 A | 5/1999 | Anderhub et al. | |
| 5,911,036 A | 6/1999 | Wright et al. | |
| 5,920,395 A | 7/1999 | Schulz | |
| 5,931,832 A | 8/1999 | Jensen | |
| 5,950,629 A | 9/1999 | Taylor et al. | |
| 5,951,475 A | 9/1999 | Gueziec et al. | |
| 5,951,587 A | 9/1999 | Qureshi et al. | |
| 5,954,731 A | 9/1999 | Yoon | |
| 5,957,902 A | 9/1999 | Teves | |
| 5,980,782 A | 11/1999 | Hershkowitz et al. | |
| 5,984,932 A | 11/1999 | Yoon | |
| 6,001,108 A | 12/1999 | Wang et al. | |
| 6,024,695 A | 2/2000 | Taylor et al. | |
| 6,063,095 A * | 5/2000 | Wang et al. | 606/139 |
| 6,080,181 A | 6/2000 | Jensen et al. | |
| 6,102,850 A * | 8/2000 | Wang et al. | 600/102 |
| 6,106,511 A | 8/2000 | Jensen | |
| 6,120,433 A | 9/2000 | Mizuno et al. | |
| 6,132,368 A | 10/2000 | Cooper | |
| 6,167,328 A * | 12/2000 | Takaoka et al. | 700/264 |
| 6,179,829 B1 | 1/2001 | Bisch et al. | |
| 6,201,984 B1 | 3/2001 | Funda et al. | |
| 6,206,903 B1 | 3/2001 | Ramans | |
| 6,223,100 B1 | 4/2001 | Green | |
| 6,226,566 B1 | 5/2001 | Funda et al. | |
| 6,231,526 B1 | 5/2001 | Taylor et al. | |
| 6,233,504 B1 * | 5/2001 | Das et al. | 700/260 |
| 6,244,809 B1 | 6/2001 | Wang et al. | |
| 6,246,200 B1 | 6/2001 | Blumenkranz et al. | |
| 6,259,806 B1 | 7/2001 | Green | |
| 6,292,712 B1 * | 9/2001 | Bullen | 700/245 |
| 6,309,397 B1 | 10/2001 | Julian et al. | |
| 6,312,435 B1 | 11/2001 | Wallace et al. | |
| 6,323,837 B1 | 11/2001 | Rosenberg | |
| 6,331,181 B1 | 12/2001 | Tierney et al. | |
| 6,346,072 B1 | 2/2002 | Cooper | |
| 6,364,888 B1 | 4/2002 | Niemeyer et al. | |
| 6,371,952 B1 | 4/2002 | Madhani et al. | |
| 6,385,509 B2 * | 5/2002 | Das et al. | 700/260 |
| 6,424,885 B1 | 7/2002 | Niemeyer et al. | |
| 6,565,554 B1 | 5/2003 | Niemeyer | |
| 6,587,750 B2 | 7/2003 | Gerbi et al. | |
| 6,592,315 B2 * | 7/2003 | Osborne, Jr. | 414/9 |
| 6,594,552 B1 | 7/2003 | Nowlin et al. | |
| 6,697,044 B2 * | 2/2004 | Shahoian et al. | 345/156 |
| 6,728,599 B2 * | 4/2004 | Wang et al. | 700/258 |
| 6,793,653 B2 * | 9/2004 | Sanchez et al. | 606/1 |
| 6,837,883 B2 * | 1/2005 | Moll et al. | 606/1 |
| 6,928,490 B1 * | 8/2005 | Bucholz et al. | 709/249 |
| 2001/0000663 A1 * | 5/2001 | Shahoian et al. | 345/156 |
| 2001/0020200 A1 * | 9/2001 | Das et al. | 700/260 |
| 2001/0027312 A1 | 10/2001 | Bacher et al. | |
| 2002/0045887 A1 * | 4/2002 | DeHoogh et al. | 606/1 |
| 2002/0120252 A1 | 8/2002 | Brock et al. | |
| 2003/0040758 A1 * | 2/2003 | Wang et al. | 606/130 |
| 2003/0050649 A1 * | 3/2003 | Brock et al. | 606/130 |
| 2003/0109857 A1 * | 6/2003 | Sanchez et al. | 606/1 |
| 2005/0113946 A9 * | 5/2005 | Janik | 700/94 |

FOREIGN PATENT DOCUMENTS

| | | |
|---|---|---|
| DE | 4310842 | 1/1995 |
| EP | 239409 | 9/1987 |
| EP | 424687 | 5/1991 |
| EP | 776738 | 6/1997 |
| WO | WO-9104711 | 4/1991 |
| WO | WO-9220295 | 11/1992 |
| WO | WO-9313916 | 7/1993 |
| WO | WO-9418881 | 9/1994 |
| WO | WO-9426167 | 11/1994 |
| WO | WO-9715240 | 5/1997 |
| WO | WO-9825666 | 6/1998 |
| WO | WO-03049596 A2 | 6/2003 |

OTHER PUBLICATIONS

Abstract of a presentation "3 D Vision Technology Applied to Advanced Minimally Invasive Surgery Systems," (Session 15/3) given at the 3rd World Congress of Endoscopic Surgery in Bordeaux, Jun. 18-20, 1992, (1 page total).

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992, (1 page total).

Abstract of a presentation "Concept and Experimental Application of a Surgical Robotic System the Steerable MIS Instrument SMI," given at the 3rd World Congress of Endoscopic Surgery in Bordeaux, Jun. 18-20, 1992, 1 page total.

Abstract of a presentation given at the 3rd World Congress of Endoscopic Surgery in Bordeaux entitled "Session 15/1", Jun. 18-20, 1992.

Abstract of a presentation given at the 3rd World Congress of Endoscopic Surgery in Bordeaux entitled "Session 15/4", Jun. 18 to 20, 1992, (1 page total).

Abstract of a presentation given at the 3rd World Congress of Endoscopic Surgery in Bordeaux entitled "Session 15/5", Jun. 18 to 20, 1992, (1 page total).

Abstract of a presentation given at the 3rd World Congress of Endoscopic Surgery in Bordeaux, entitled "Session 15/2", Jun. 18-20, 1992, 1 page total.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1973, pp. 121-136, vol. 2, Springer-Verlag.

Alexander, Arthur D., "A Survey Study of Teleoperators Robotics and Remote Systems Technology," Remotely Manned Systems—Exploration and Operation in Space, California Institute of Technology, 1973.

Bejczy, Antal K. et al., "Controlling Remote Manipulators through Kinesthetic Coupling," Computers in Mechanical Engineering, 1983, pp. 48-60, vol. 1—Issue 1.

Ben Gayed et al., "An Advanced Control Micromanipulator for Surgical Applications," Systems Science, 1987, pp. 123-134, vol. 13.

Besant, Colin et al., Abstract of presentation "Camera Control for Laparoscopic Surgery by Speech recognizing Robot: Constant Attention and Better Use of Personnel," 3rd World Congress of Endoscopic surgery, 1993, p. 271, vol. 3—issue 3.

Charles, Steve et al., "Design of a Surgeon Machine Interface for Teleoperated Microsurgery," Proceedings of IEEE Annual Conference on Engineering in Medicine and Biology, 1989, pp. 0883-0884, vol. 11, IEEE.

Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.

Corcoran, Elizabeth, "Robots for the Operating Room," The New York Times, 2 pages total, Jul. 19, 1992, Section 3 p. 9C.

Das, Hari et al., "Kinematic Control and Visual Display of Redundant Teleoperators," IEEE International Conference on Systems, Man, and Cybernetics, 1989, pp. 1072-1077, vol. 3, IEEE.

Dolan J.M. et al., "A Robot in an Operating Room: A Bull in a China Shop," 1987, pp. 1096-1097, vol. 2.

Green, Philip S. et al., Abstract of a presentation "Telepresence: Advanced Teleoperator Technology for Minimally Invasive Surgery," given at the 3rd World Congress of Endoscopic Surgery in Bordeaux, Jun. 18-20, 1992, 2 pages total.

Green, Philip S. et al., Abstract of a presentation, "Telepresence: Advanced Teleoperator Technology for Minimally Invasive Surgery," 1992 Medicine Meets Virtual Reality (MMVR) symposium in San Diego, Jun. 4-7, 1992, 1 page.

Green, Philip S. et al., Statutory Declaration by Dr. Phillip S. Green, the presenter of the video entitled "Telepresence Surgery: The Future of Minimally Invasive Medicine," European Patent Convention in the Matter of EP-B-653922. 32 pages, Sep. 12, 2000.

Guerrouad, Aicha et al., "SMOS: Stereotaxical Microtelemanipulator for Ocular Surgery," IEEE Engineering in Medicine and Biology Society 11th annual international conference, Nov. 9-12, 1989, pp. 879-880, vol. 3, IEEE.

Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.

Inoue, Masao; "Six-Axis bilateral control of an articulated slave manipulator using a Cartesian master manipulator," Advanced robotics, 1990, pp. 139-150, vol. 4—Issue 2, Robotic society of Japan.

Jackson, Bernie G. et al., "Force Feedback and Medical Simulation," Interactive Technology and the New Paradigm for Healthcare, Morgan et al (Eds ), 1995, pp. 147-151, vol. 24, IOS Press and Ohms.

Jau, B. M., "Anthropomorphic Remote Manipulator," NASA Tech Briefs, Apr. 1991, pp. 92, NASA's Jet Propulsion Laboratory, Pasadena, California.

Kazerooni, H., "Human/Robot Interaction via the Transfer of Power and Information Signals Part I: Dynamics and Control Analysis," IEEE International Conference on Robotics and Automation, 1989, pp. 1632-1640, IEEE.

Krishnan, S.M. et al., Abstract of a presentation "Design Considerations of a New Generation Endoscope Using Robotics and Computer Vision Technology," given at the 3rd World Congress of Endoscopic Surgery in Bordeaux, Jun. 18-20, 1992, (1 page total).

Lavallee, Stephane, "A New System for Computer Assisted Neurosurgery," IEEE Eng. in Med. and Biol. Soc. 11th Annual International Conference, Jun. 1989, pp. 926-927, vol. 11.

Mair, Gordon M., Industrial Robotics, Prentice Hall, 1988, pp. 41-43, 49-50, 54, 203-209.

Majima S. et al., "On a Micro Manipulator for Medical Application Stability Consideration of its Bilateral Controller Mechatronics," 1991, pp. 293-309, vol. 1—Issue 3.

Preising, B. et al., "A Literature Review: Robots in Medicine," IEEE Engineering in Medicine and Biology, 1991, pp. 13-22, 71, vol. 10—Issue 2, IEEE.

Rasor, Ned S. et al., "Endocorporeal Surgery Using Remote Manipulators," Proceedings of the First National Conference held at California Institute of Technology, 1973, pp. 483-492.

Taubes, Gary et al., "Surgery in Cyberspace," Discover magazine, Dec. 1994, vol. 15, issue 12, pp. 85-92.

Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.

Tejima, Noriyuki et al., "A New Microsurgical Robot System for Corneal Transplantation," Precision Machinery, 1988, pp. 1-9, vol. 2, Gordon and Breach Science Publishers Inc.

Tendick, Frank et al., "Analysis of the Surgeon's Grasp for Telerobotic Surgical Manipulation," IEEE 11th Annual Int Conf on Engineering in Medicine and Biology, Jun. 1989, pp. 914-915, IEEE.

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited.

Transcript of a video presented by SRI at the 3rd World Congress of Endoscopic Surgery in Bordeaux, France on Jun. 18-20, 1992; in Washington D.C. on Apr. 9, 1992; and in San Diego, CA on Jun. 4-7, 1992; entitled "Telepresence Surgery: The Future of Minimally Invasive Medicine," 3 pages.

Trevelyan, James P. et al., "Motion Control for a Sheep Shearing Robot," IEEE Robotics Research Conference, the 1st International Symposium, Carroll, NH, USA., 1983, pp. 175-190, MIT Press.

Vibet, C., "Properties of Master Slave Robots," Motor-con, 1987, pp. 309-316.

Wolf, Stanley et al., Student Reference Manual for Electronic Instrumentation Laboratories, 1990, pp. 498 and 499, Prentice Hall New Jersey.

EP-02799211.4 Supplementary Partial European Search Report dated Aug. 21, 2009, 4 pages.

EP02799211.4 Office Action dated May 20, 2010, 5 pages.

\* cited by examiner

FIG. 3

MULTIFUNCTIONAL HANDLE FOR A MEDICAL ROBOTIC SYSTEM

CROSS-REFERENCES TO RELATED APPLICATIONS

This is a continuation patent application which claims priority from U.S. patent application Ser. No. 10/012,602 filed Dec. 8, 2001, now U.S. Pat. No. 6,793,653, the full disclosure of which is incorporated herein by reference.

BACKGROUND OF THE INVENTION

1. Field of the Invention

The present invention relates to a multi-function button on a handle that is used to control a robotically controlled medical instrument.

2. Background Information

Historically, surgery has been performed by making large incisions in a patient to provide access to the surgical site. There has been developed instruments that allow a surgeon to perform a procedure through small incisions in the patient. The instruments include an endoscope which has a camera that allows the surgeon to view the internal organs of the patient through a small incision. Such procedures are less traumatic to the patient and have shorter recovery times than conventional surgical procedures. Endoscopic instruments have even been used to perform minimally invasive heart surgery. Blockage of a coronary artery may deprive the heart of blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform a minimally invasive surgery, including CABG procedures. The procedure is performed with instruments that are inserted through small incisions in the patient's chest. The instruments are controlled by robotic arms. Movement of the robotic arms and actuation of instrument end effectors are controlled by the surgeon through a pair of handles that are coupled to an electronic controller. The surgeon can control the movement of an endoscope used to view the internal organs of the patient through voice commands and speech recognition software.

Each medical instrument may have a plurality of functions such as motion scaling and grasper actuation. Each function requires a separate input from the end user. For example, motion scaling requires that the user pull up a corresponding graphical user interface in the system and select a desired scale. To change the scale, the surgeon must release the handles and move over to the device and/or screen. Releasing the handles may result in an undesirable movement of the medical instruments. Additionally, having to release the handles and select the scale increases the time to perform the procedure. It would be desirable to allow the surgeon to control a function without releasing the handles.

BRIEF SUMMARY OF THE INVENTION

A handle for a medical robotic system. The handle may include a pair of buttons attached to a handle housing. One of the buttons may be used to control a selected function of a medical instrument.

BRIEF DESCRIPTION OF THE DRAWINGS

FIG. 3 is a perspective view of a handle assembly of the robotic system used to control a medical instrument;

DETAILED DESCRIPTION OF THE INVENTION

Disclosed is a handle used to control movement of a medical instrument. The medical instrument may be coupled to a robotic arm that is connected to a controller. The medical instrument may have a plurality of functions such as wrist locking and motion scaling. One of the functions may be selected through a graphical user interface operated by the end user. The handle may have a plurality of buttons. One of the buttons may allow the end user to control the selected function. For example, when wrist locking/unlocking is selected, depressing the button can toggle the medical instrument wrist between a locked state and an unlocked state.

Figure 1:
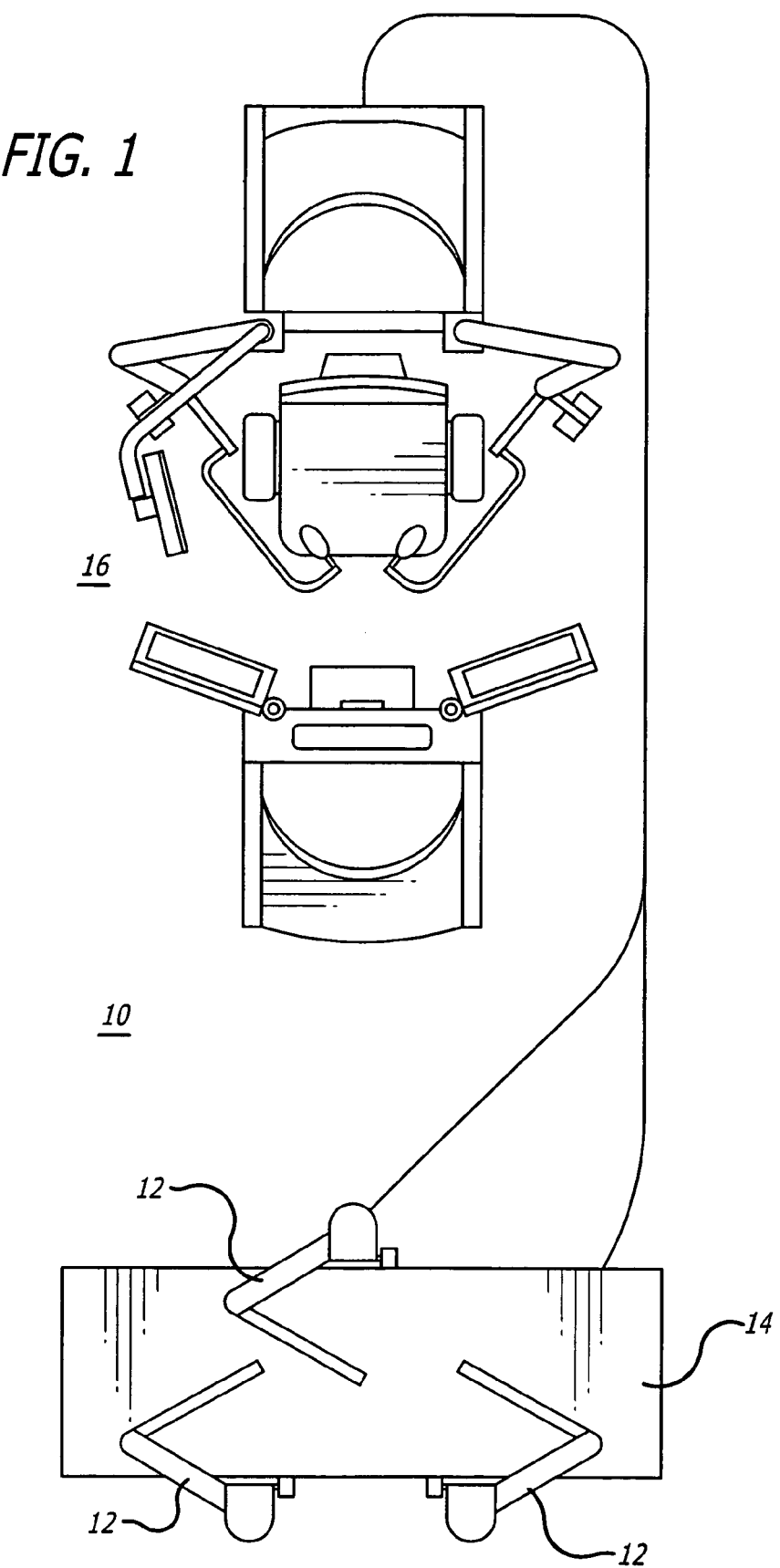
FIG. 1 is a top view of an illustration of a robotic system.

Referring to the drawings more particularly by reference numbers, FIG. 1 shows a robotic system 10. The system 10 may include a plurality of robotic arms 12 located adjacent to a table 14. Two of the robotic arms 12 may control the movement of corresponding medical instruments (not shown). The third robotic arm 12 may control the movement of an endoscope (not shown). The robotically controlled instruments and endoscope may be used to perform a minimally invasive medical procedure on a patient-lying on the table 14.

The robotic arms 12 and accompanying instruments may be the same or similar to robotic products sold by Computer Motion under the trademarks AESOP and ZEUS. Although three robotic arms 12 are shown and described, it is to be understood that the system 10 may have a different number of arms 12.

The robotic arms 12 are controlled by a "surgeon" area 16. The surgeon area 16 may be located adjacent to the table 14. Alternatively, the surgeon area 16 may be coupled to the robotic arms 12 through a telecommunications link to allow a surgeon to have remote input into the system 10.

Figure 2:
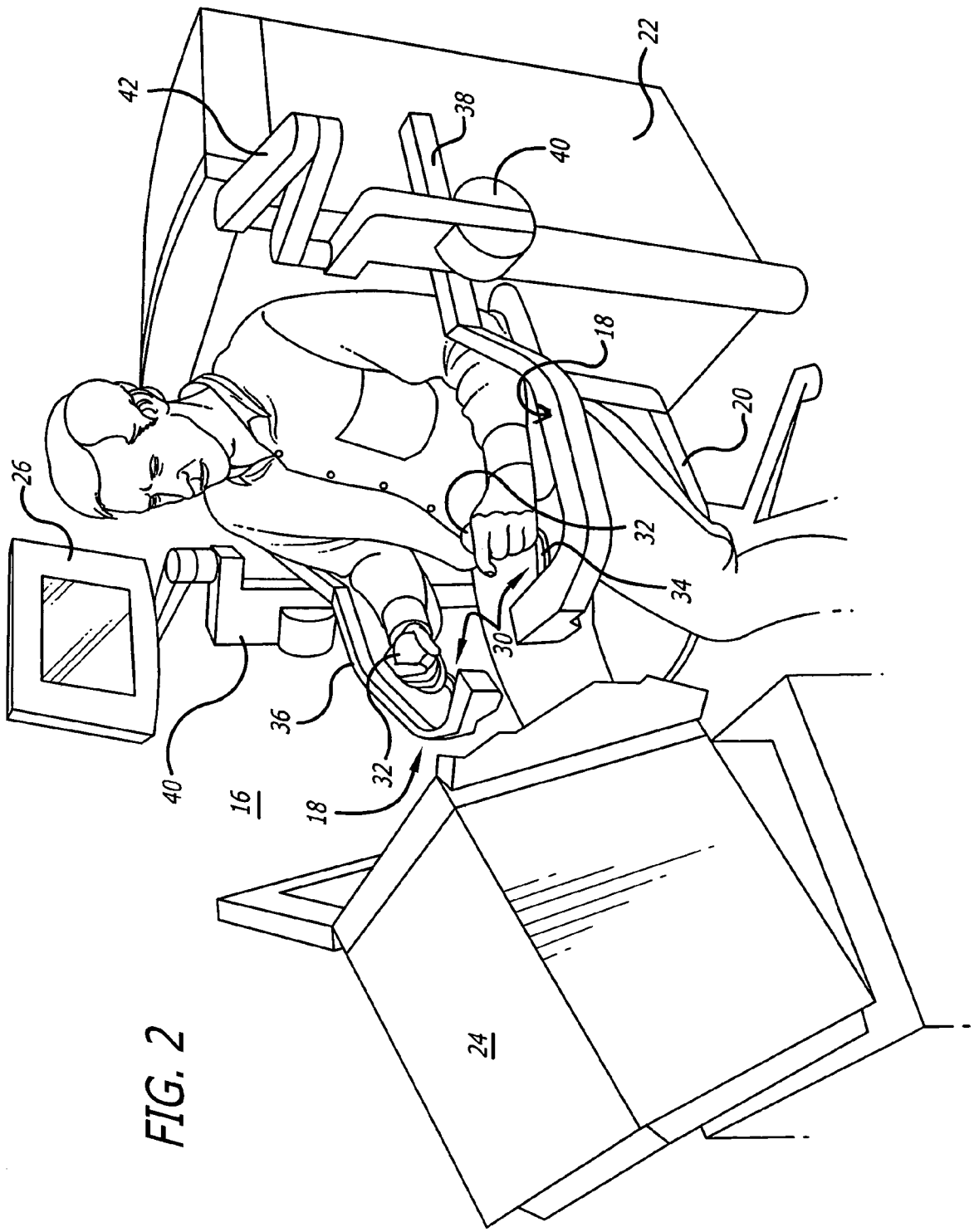
FIG. 2 is a perspective view of a surgeon control area of the robotic system.

FIG. 2 shows a surgeon area 16. The surgeon area 16 includes a pair of handle assemblies 18 located adjacent to a surgeon's chair 20. The handle assemblies 18 are coupled to a controller 22 that is also coupled to the robotic arms 12 and medical instruments. The controller 22 may include one or more microprocessors, memory devices, drivers, etc. that convert input information from the handle assemblies 18 into output control signals which move the robotic arms and/or actuate the medical instruments.

The surgeon's chair 20 and handle assemblies 18 may be in front of a video console 24. The video console 24 may be linked to the endoscope to provide video images of the patient. The surgeon's area 16 may also include a computer screen 26 coupled to the controller 22. The screen 26 may display graphical user interfaces (GUIs) that allow the surgeon to control various functions and parameters of the system 10.

Each handle assembly 18 may include a handle/wrist assembly 30. The handle/wrist assembly 30 has a handle 32 that is coupled to a wrist 34. The wrist 34 is connected to a forearm linkage 36 that slides along a slide bar 38. The slide bar 38 is pivotally connected to an elbow joint 40. The elbow joint 40 is pivotally connected to a shoulder joint 42 that is attached to the controller 22.

Figure 3:
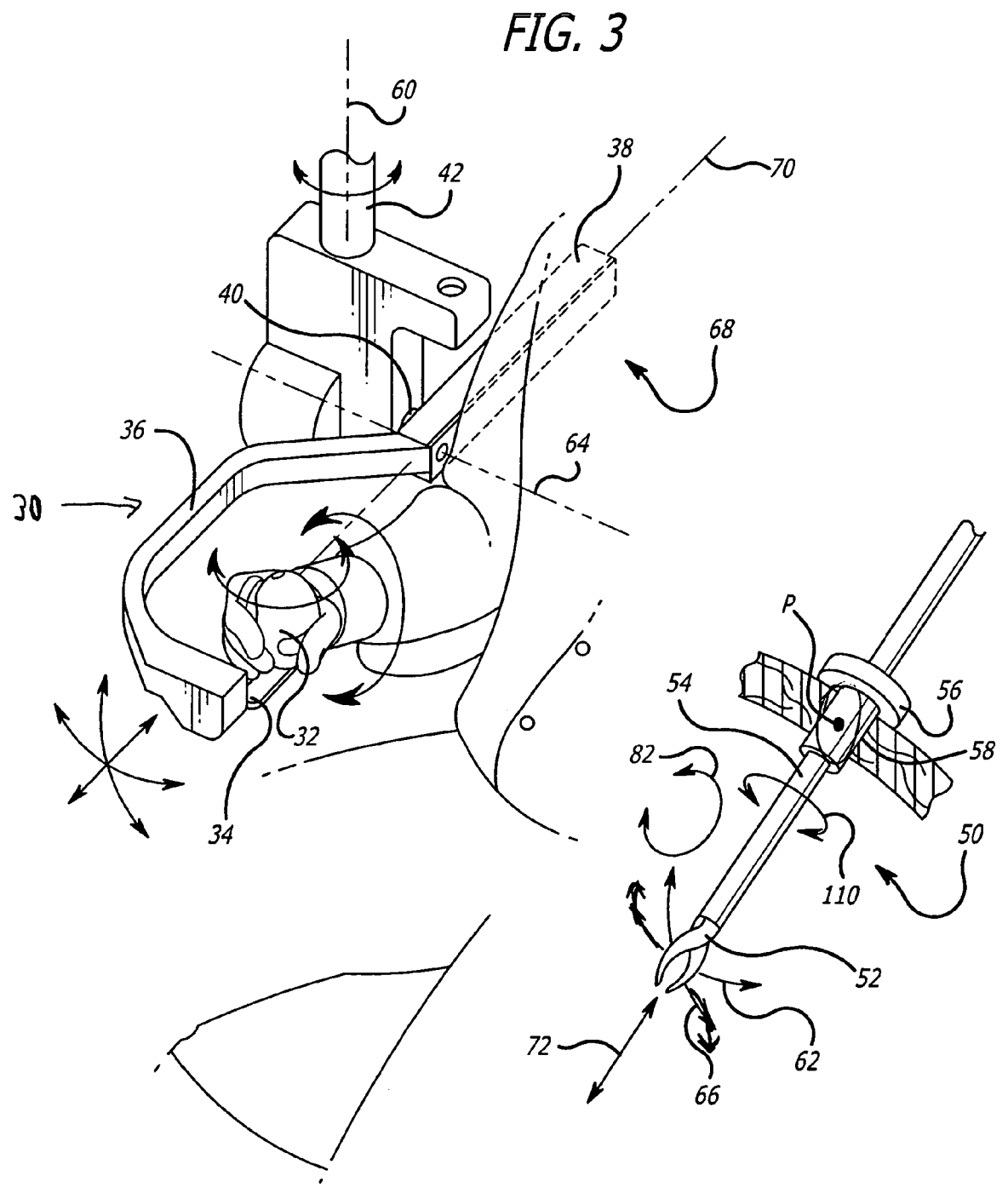

FIG. 3 shows a handle assembly 30 superimposed with a medical instrument 50. The instrument 50 includes an end effector 52 attached to an instrument shaft 54. The shaft 54 extends through a cannula 56 inserted through an incision of a patient 58. The incision defines a pivot point P for the medical instrument 50.

The shoulder joint 42 includes a sensor (not shown) that provides feedback on the movement of the handle about a shoulder axis 60. The sensor may be a mechanical encoder, optical encoder, etc. or other device which provides an output signal that corresponds to a position of the handle 32 about the shoulder axis 60. The output of the shoulder sensor is provided to the controller 22. The controller 22 performs a series of computations to determine a corresponding movement of the medical instrument 50. The computations may include one or more transformation and kinematic equations. The controller 22 provides output signals to the corresponding robotic arm 12 to move the instrument 50 as indicated by the arrows 62.

The elbow joint 40 includes a sensor (not shown) that provides positional feedback on the position of the assembly about an elbow axis 64. The controller 22 utilizes the positional feedback to drive the robotic arm and move the instrument in the direction indicated by the arrows 66.

The forearm linkage 36 and slide bar 38 create a translator 68 that allows linear movement of the linkage 36 along a translator axis 70. The translator axis 70 intersects with the axes 60 and 64. The translator 68 has a sensor (not shown) that provides feedback information that is used to drive the robotic arm and move the instrument 50 in the direction indicated by the arrows 72.

When transforming movement of the handle 32 to movement of the instrument 50 the controller 22 may equate the intersection of the axes 60, 64 and 70 to the instrument pivot point P. Equating the intersection of the axis 60, 64 and 70 with the pivot point P provides a kinematic relationship such that the surgeon "feel" like they are actually moving the instrument 50. Additionally, the length of the forearm linkage and location of the handle are such that the surgeon is provided with the sensation that they are holding and moving the distal end of the instrument. These relationships also improve the ergonomics of the handle assembly and the ease of use of the robotic system as a whole. The transformation and kinematic equations may be similar to the equations used in the AESOP and ZEUS products with the signs (+/−) reversed to account for the elbow axis 64 being behind the surgeon.

The handle assembly 18 has only five degrees of freedom; handle spin, wrist, translator, elbow and shoulder. Having only five degrees of freedom reduces the complexity of the system 10. The medical instrument 50 thus only needs a wrist with one degree of freedom which reduces the complexity, size and corresponding cost of the instrument. The configuration of the handle assembly allows the surgeon to perform any movement of the instrument with only five degrees of freedom.

Figure 4:
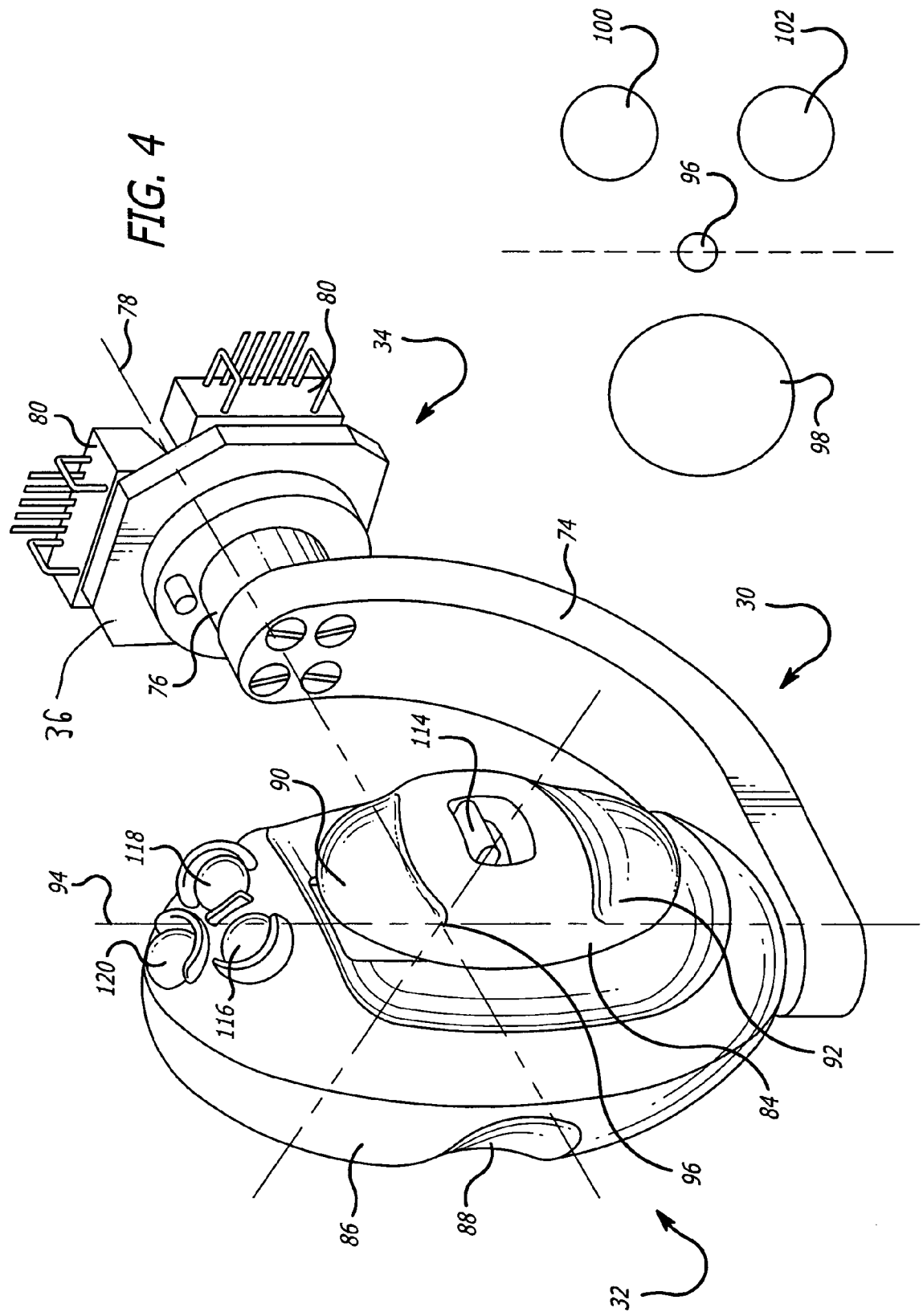
FIG. 4 is an enlarged perspective view of a wrist assembly of the robotic system controlled by a user's hand.
Figure 5:
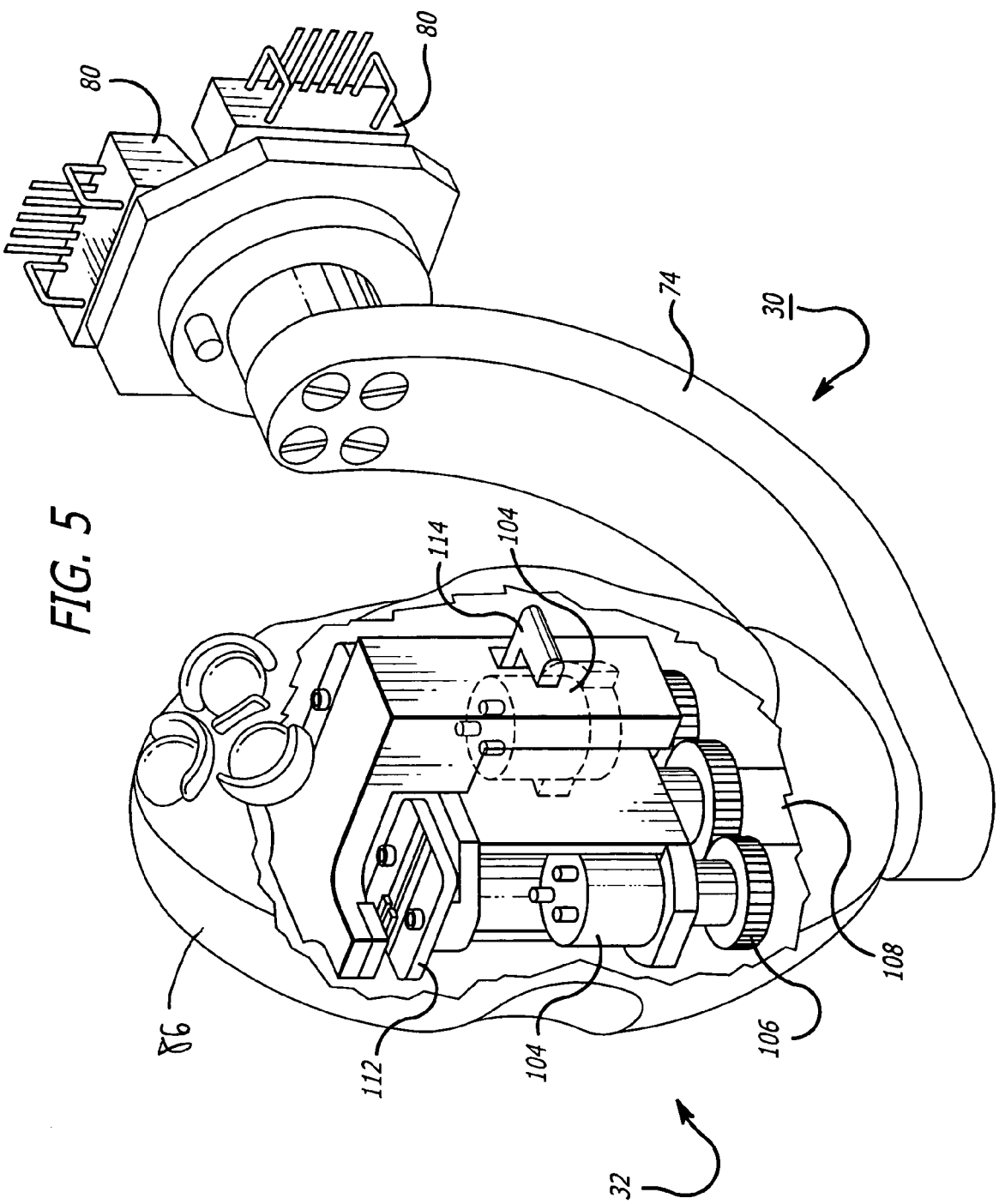
FIG. 5 is a sectional perspective view of the handle/wrist assembly.

FIGS. 4 and 5 show the wrist/handle assembly 30. The wrist 34 includes a joint shaft 74 that is coupled to the forearm linkage 36 by a roll bearing 76. The roll bearing 76 allows the handle 32 to rotate about a roll axis 78. The wrist 34 may further include sensor 80 that provides positional feedback to the controller 22. Movement of the handle 32 about the roll axis 78 may cause a corresponding rotation of the instrument end effector 52 in the direction indicated by the arrows 82 in FIG. 3.

The handle 32 includes a grasper 84 that is coupled to a handle housing 86. The housing 86 and grasper 84 are preferably shaped as an ellipsoid to allow the user to more easily grab the handle 34 with their hand. The housing 86 may have a thumb groove 88 that receives the user's thumb. The grasper 84 may have a pair of grooves 90 and 92 to receive the index and middle fingers of the user, respectively.

The handle 32 can rotate about a wrist axis 94. To improve the ergonomics of the wrist/handle assembly 30 the wrist axis 94 preferably intersects the roll axis 78 at a centroid 96 located between the thumb 98, index finger 100 and middle finger 102 of the user's hand. It has been found that such a configuration creates a more ergonomically correct feel of the handle 32 and movement of the wrist/handle assembly 30. The wrist 34 may include sensor 104 that provides positional feedback information to the controller 22 which is used to spin the medical instrument 50 as indicated by the arrows 82 in FIG. 3.

The grasper 84 can be depressed by user. The grasper 84 is coupled to a sensor 112 which provides feedback information to the controller 22. The feedback information is used by the controller 22 to actuate the end effector 52 shown in FIG. 3. By way of example, depressing the grasper 84 may close the end effector 52. The grasper 84 may include a switch 114 that allows the user to lock the position of the grasper 84 and the end effector 52 of the corresponding medical instrument.

The handle 32 have a plurality of buttons 116, 118 and 120 that can be depressed by the user. By way of example, button 116 may be used to activate a cutting mode on a cauterizing end effector. Button 118 may be used to activate a coagulating medical instrument.

The button 120 may be used to vary different functions of the system. The function being controlled by the button 120 is pre-selected by the end user through an input device. The input device may be a graphical user interface (GUI) displayed by the computer screen 26. Although a graphical user interface is shown and described, it is to be understood that other input devices such as a voice recognition interface, keypads, etc. can be used to select the function that is to be controlled by the button 120.

Figure 6:
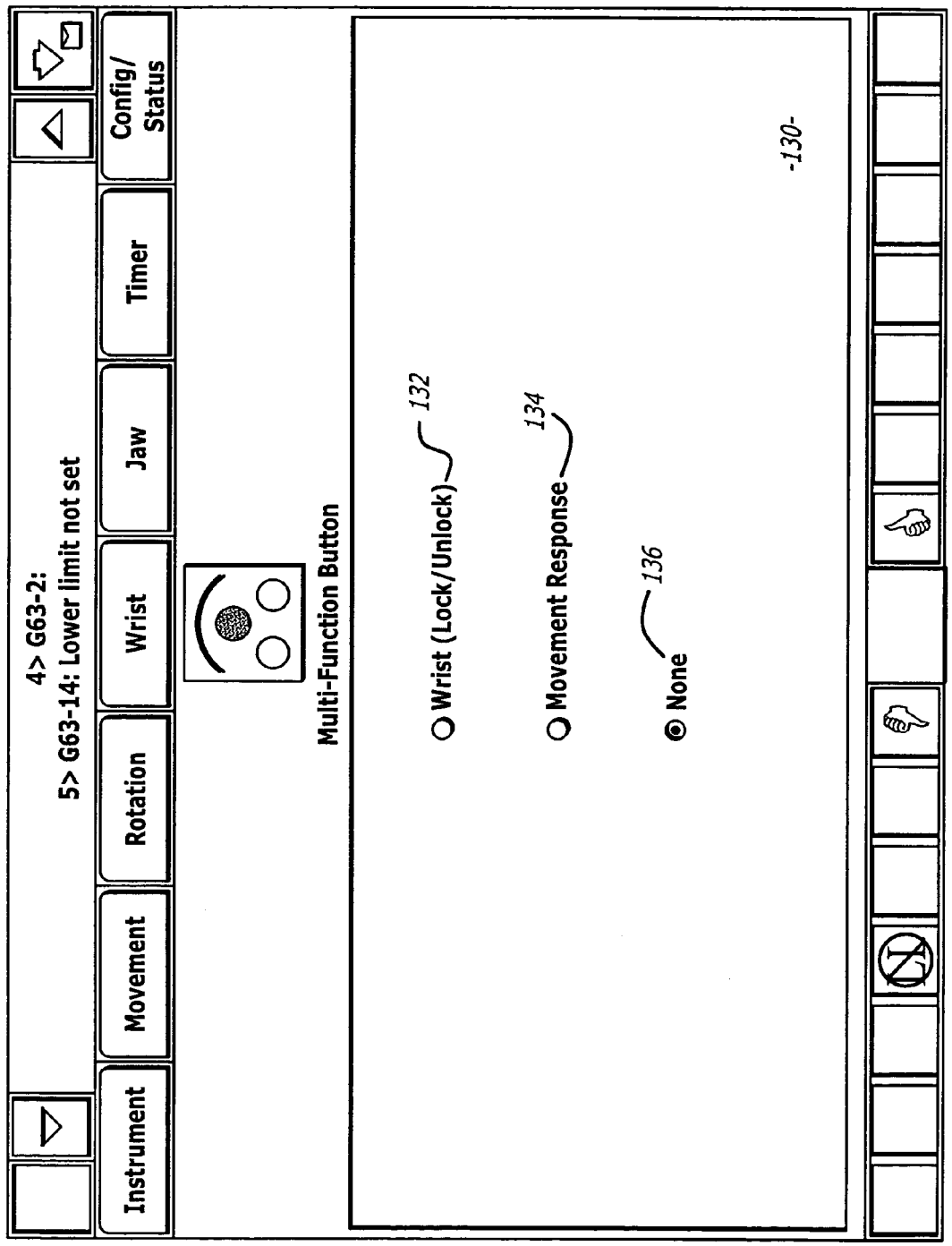
FIG. 6 is front view of a graphical user interface used to select an instrument function for a multi-function button of the system handles.

FIG. 6 shows a graphical user interface 130 used to select the function controlled by the button 120. In this example, two different functions can be selected; Wrist (Lock/Unlock) 132 and Movement Response 134. Wrist (Locked/Unlocked) 132 allows the surgeon to lock and unlock the wrist joint of the medical instrument by depressing the button 120. Movement Response 134 allows the surgeon to vary the motion scaling of the system. Motion scaling varies the corresponding movement of the handles and the medical instrument. For example, the scale may be set so that an incremental movement of the handles causes a corresponding movement of the medical instrument that is one-half the incremental handle movement (i.e. 1:0.5 scale).

The graphical user interface 130 allows the end user to select one of the functions. The multi-function buttons 120 of each handle can be driven inactive by selecting None 136 on the graphical user interface 130. The function input can be provided through a keyboard, mouse, voice recognition or any other input device for the system and GUI 130.

Once the function is selected the button 120 for each handle will control that function for the corresponding medical instrument. For example, if Wrist (Lock/Unlock) 132 is selected then depressing the button 120 of the right hand handle will lock the wrist of the corresponding medical instrument. Depressing the button 120 will again unlock the wrist. Likewise, depressing the button 120 on the left hand handle will lock the wrist of the other medical instrument. The multi-function buttons 120 allow the surgeon to lock/unlock the wrist without having to move their hands from the handle. A feature that reduces both the time and complexity of using the system to perform a medical procedure. motion scaling of the system with the multi-function buttons 120. For example, depressing one or both multi-function buttons 120 may change the motion scale from "low" to "medium". Depressing the buttons 120 again may change the scale from "medium" to "high". Further button 120 manipulation may change the scale from "high" to "low". The multi-function buttons again allow the surgeon to control a function of the system without removing their hands from the handles.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical robotic system comprising:
   a medical instrument;
   a control input device constructed so as to be grippable by a hand of a user while being manipulated by the hand of the user to command corresponding movement of the medical instrument, the control input device having a switch mechanism positioned on the control input device so as to be switchable by a digit of the hand of the user without releasing a grip of the control input device when the hand of the user is gripping the control input device;
   a computer screen having a graphical user interface for user selection of a selected function for the switch mechanism from a plurality of user selectable functions including motion scaling; and
   a controller configured to control robotic movement of the medical instrument in response to user manipulation of the control input device and alter such controlled movement by applying a motion scale factor selected by the user from a set of at least three motion scale factors of different magnitudes, wherein an actuation of the switch mechanism by the user changes the applied motion scale factor to the next motion scale factor in the set, while controlling the robotic movement of the medical instrument in response to the user manipulation of the control input device and when the selected function is motion scaling to scale corresponding movement of the control input device and the medical instrument.

2. The medical robotic system of claim 1, wherein the medical instrument comprises end effector jaws, and the control input device comprises a grasper actuatable by the hand of the user when the hand is gripping the control input device so that the end effector jaws close in response to actuation of the grasper.

3. The medical robotic system of claim 1, wherein the medical instrument comprises a wrist coupling an end effector to a shaft, the plurality of selectable functions includes wrist locking, and the controller is configured to lock and unlock the wrist according to a state of the switch mechanism when the selected function is wrist locking.

4. The medical robotic system of claim 1, wherein the control input device has a plurality of manually operable buttons, and the switch mechanism comprises one of the plurality of manually operable buttons.

5. The medical robotic system of claim 1, further comprising:
   an image capturing device; and
   a video console coupled to the image capturing device so as to display images captured by the image capturing device while the user robotically manipulates the medical instrument through the control input device.

6. The medical robotic system of claim 1, wherein the plurality of user selectable functions is identified on the computer screen, and further comprising:
   a user manipulatable input device associated with the graphical user interface so as to facilitate user selection of one of the plurality of user selectable functions identified on the computer screen.

7. The medical robotic system of claim 1, wherein the plurality of user selectable functions is identified on the computer screen, and further comprising:
   a voice activated mechanism associated with the graphical user interface so as to facilitate user selection of one of the plurality of user selectable functions identified on the computer screen.

* * * * *